United States Patent [19]

Esposito et al.

[11] Patent Number: 5,271,904
[45] Date of Patent: Dec. 21, 1993

[54] APPARATUS FOR SENSING A CHEMICAL PROPERTY OF A SPRAY

[75] Inventors: Albert J. Esposito, Amherst, N.Y.; Stuart M. Dalton, Menlo Park, Calif.; Gary M. Andes, Lockport; Gerard B. Maybach, Appleton, both of N.Y.

[73] Assignee: Electric Power Research Institute, Inc., Palo Alto, Calif.

[21] Appl. No.: 947,000

[22] Filed: Sep. 17, 1992

[51] Int. Cl.$^5$ .............................................. G05B 1/06
[52] U.S. Cl. ..................................... 422/105; 422/62; 422/63; 422/108; 436/119; 436/163; 204/400; 55/220
[58] Field of Search ............... 422/62, 63, 105, 108; 204/400, 409, 420, 428, 433, 153.21; 55/220; 436/163, 119

[56] References Cited

U.S. PATENT DOCUMENTS

| | | | |
|---|---|---|---|
| 4,016,063 | 4/1977 | Radnoti | 204/195 R |
| 4,240,798 | 12/1980 | Wendelin et al. | 422/62 X |
| 4,354,308 | 10/1982 | Shimada et al. | 204/400 X |
| 4,383,908 | 5/1983 | Phelps et al. | 204/409 |
| 4,388,283 | 6/1983 | Abrams et al. | 423/242 |
| 4,401,548 | 8/1983 | Brezinski | 204/435 |
| 4,427,643 | 1/1984 | Fowler | 422/62 X |
| 4,537,661 | 8/1985 | Lee et al. | 204/428 X |
| 4,664,772 | 5/1987 | Zaccari et al. | 204/400 |
| 4,683,049 | 7/1987 | Nakajima et al. | 204/428 |
| 4,767,995 | 8/1988 | Berry | 204/409 X |
| 4,786,398 | 11/1988 | Wertheimer et al. | 204/428 X |
| 4,818,364 | 4/1989 | Weber et al. | 204/427 |
| 4,832,915 | 5/1989 | Messura et al. | 422/62 |
| 4,966,711 | 10/1990 | Hoots et al. | 210/697 |
| 4,966,757 | 10/1990 | Lewis et al. | 422/62 |
| 5,008,203 | 4/1991 | Mathews | 436/55 |
| 5,098,667 | 3/1992 | Young et al. | 422/111 |
| 5,139,641 | 8/1992 | Neukum | 204/435 |
| 5,147,524 | 9/1992 | Broadley | 204/433 |
| 5,168,065 | 12/1992 | Jankura et al. | 436/55 |
| 5,171,450 | 12/1992 | Hoots | 210/701 |

Primary Examiner—James C. Housel
Assistant Examiner—Harold Y. Pyon
Attorney, Agent, or Firm—James W. Maccoun

[57] ABSTRACT

A sheath is used to house a conventional pH sensor within the sheath's interior. The sheath is exposed to a descending spray within a sulfur dioxide ($SO_2$) absorber. A fill port collects a portion of the spray and the sheath accumulates the collected spray as a slurry sample within its interior. The pH sensor becomes immersed in the sample slurry. Slurry is discharged from the interior by way of drain notches and drain holes. Discharged sample slurry descends to enter a bulk slurry to allow recycling. A steady state of slurry collection and slurry discharge is reached such that the sample slurry is continuously refreshed. Elevation of the sheath over the bulk slurry prevents slurry from the bulk from entering into the slurry sample.

23 Claims, 4 Drawing Sheets

APPARATUS FOR SENSING A CHEMICAL PROPERTY OF A SPRAY

BACKGROUND OF THE INVENTION

1. Field of Invention

This invention relates to an apparatus for sensing chemical properties of sprays used in flue gas desulfurization systems. More specifically, this invention relates a novel apparatus used to house a conventional sensor for sensing the pH of a spray that is used to absorb sulfur dioxide from flue gas produced by coal combustion.

2. Description of the Related Art

This invention relates to process control of systems which remove sulfur dioxide ($SO_2$) from flue gas produced by coal combustion; more specifically, it relates to absorbers in which $SO_2$ laden gas passes through a spray of finely divided limestone or lime in aqueous solution. This spray is introduced into absorbers by sprayers that convert fluid in the form of a slurry into a spray. $SO_2$ is present in waste gases generated from combustion of fossil fuels, for example, in electrical power generation. $SO_2$ is also generated in waste gases from metal ore processing. The two types of waste gases just mentioned are commonly referred to as "flue gases." Since $SO_2$ has long been recognized as an atmospheric pollutant, desulfurization systems are in widespread use. Even small improvements in efficiency of $SO_2$ absorbers can be highly beneficial to the public due to the large numbers of absorbers in use and due to the large volumes of flue gases processed by them.

Some desulfurization systems use bases (alkalines) to treat $SO_2$ containing gas. Finely divided limestone or lime is commonly used as the alkaline material. An example of such a desulfurization system is disclosed by U.S. Pat. No. 4,388,283 entitled "$SO_2$ REMOVAL" which patent is hereby incorporated by reference.

In limestone or lime desulfurization systems, an aqueous slurry of finely divided limestone or lime is pumped through sprayer nozzles in an absorber. The chemically active constituents (i.e., the alkaline reagents) of these sprays are calcium carbonate ($CaCO_3$) for limestone and calcium hydroxide ($CaOH$) for lime. $SO_2$ laden gas is forced into the absorber and then forced through the spray. When $SO_2$ passes through the spray, a chemical reaction occurs in which $SO_2$ combines with the alkaline reagents to form insoluble calcium sulfite ($CaSO_3$) and calcium sulfate ($CaSO_4$), and water, $H_2O$. Spray traverses a spray zone in the absorber which spray zone is the location at which $SO_2$ absorption occurs. After traversing the spray zone the spray collects as a slurry in a reaction tank from where it is recycled to be again sprayed through the spray zone. The pH and other chemical properties of the slurry to be recycled are adjusted, as desired, through addition of water and limestone.

Continuous adjustment and control of the pH of limestone spray is important since effectiveness of $SO_2$ removal is a function of spray pH. However, spray pH control is problematic since this pH depends upon factors such as natural variations in limestone, the degree of fineness to which limestone is ground, and the weight percent of limestone in the aqueous slurry. Moreover, the optimal pH varies depending upon the chemical composition of both the spray and the gas. Finally, the chemical composition of the gas varies with natural variations in the composition of fossil fuel and metal ore.

A further complication is present since the pH of particular spray droplets changes in response to reaction with flue gas as the spray droplets traverse the spray zone within the absorber. It is desirable that the spray be chemically effective throughout the spray zone rather than only effective as the spray enters the spray zone. Finally, pH must be controlled within lower and upper limits so that the spray does not become to acidic, which would cause corrosion of the absorber system, and so that the spray does not become too basic, which would cause scale formation and clogging of the system, particularly clogging of the system piping with precipitates.

In some absorption systems, the pH control point is the slurry as it is recirculated to the sprayer. That is, pH of the slurry is sensed at a recirculation line and pH is adjusted according to the pH measurement there sensed. Another pH control point is the reaction tank. However, neither of these control points provides for sensing the pH of the spray in the spray zone. Moreover, the varying pH at different locations within the spray zone is not sensed at either of those control points. The reaction tank has additional limitations as a control point since the large volume of slurry contained within it acts to heavily buffer the effects of spray having a different pH from the slurry.

The limitations mentioned in the previous paragraphs inspire a need for a novel apparatus designed to permit sensing of pH at various locations within the spray zone. In order to accurately sense pH, the sensor's electrode, that is, the sensing element of the sensor, should be completely immersed in the spray. This precludes a simple insertion of the sensor into the spray zone since such insertion would provide neither an accurate nor a reliable pH indication.

Measuring pH in the spray zone is difficult to accomplish because the spray zone is a hostile environment for a pH sensor. Spray is emitted in large quantities at high pressure and spray has abrasive constituents. The spray so emitted is not unlike the effect of a sandblasting process. Direct exposure of a sensor to this environment may result in accelerated sensor erosion requiring frequent replacement of costly sensors. The delicate nature of pH sensors also calls for sensor protection from the high slurry forces and gas turbulences that are characteristic of the spray zone.

A novel apparatus is therefore desired which will allow a conventional pH sensor to be immersed in spray at various locations within the spray zone, the key location for pH measurement in $SO_2$ absorbers, and which will protect the sensor from excessive wear and premature breakage.

SUMMARY OF THE INVENTION WITH OBJECTS

It is a general object of the invention to improve the efficiency of $SO_2$ absorbers by providing improved process control of the absorption process.

It is another object of the invention to provide an apparatus for inserting a pH sensor within the spray zone of an $SO_2$ absorber.

It is another object of the invention to provide an apparatus for inserting a pH sensor into various locations, heights, and depths within the spray zone of an $SO_2$ absorber.

It is another object of the invention to provide an apparatus for inserting a pH sensor at selectable depths into the spray zone of an $SO_2$ absorber.

It is another object of the invention to provide an apparatus which allows convenient insertion of a sensor into a spray and which allows convenient removal of the sensor from the spray.

It is still another object of the invention to provide an apparatus for protecting a delicate pH sensor from excessive wear caused by an abrasive spray.

These and other objects are accomplished with a novel sheath which is used to house a conventional pH sensor within the sheath's interior. The sheath is exposed to a descending spray within an $SO_2$ absorber. A fill port collects a portion of the spray and the sheath accumulates the collected spray as a fluid sample in the form of a slurry within the sheath's interior. As slurry accumulates within the sheath's interior, the pH sensor becomes immersed in the sample slurry. Slurry is discharged from the interior by way of drains. Discharged slurry descends to enter a bulk slurry to allow recycling in the absorption process. A steady state of spray collection and slurry discharge is reached such that the sample slurry is continuously refreshed.

While the apparatus is disclosed with respect to sensing pH in sprays of $SO_2$ absorbers, it should be understood to be equally applicable to sensing chemical properties other than pH and equally applicable to sensing chemical properties in sprays found in locations other than within $SO_2$ absorbers.

DESCRIPTION OF THE INVENTION

Figure 1:
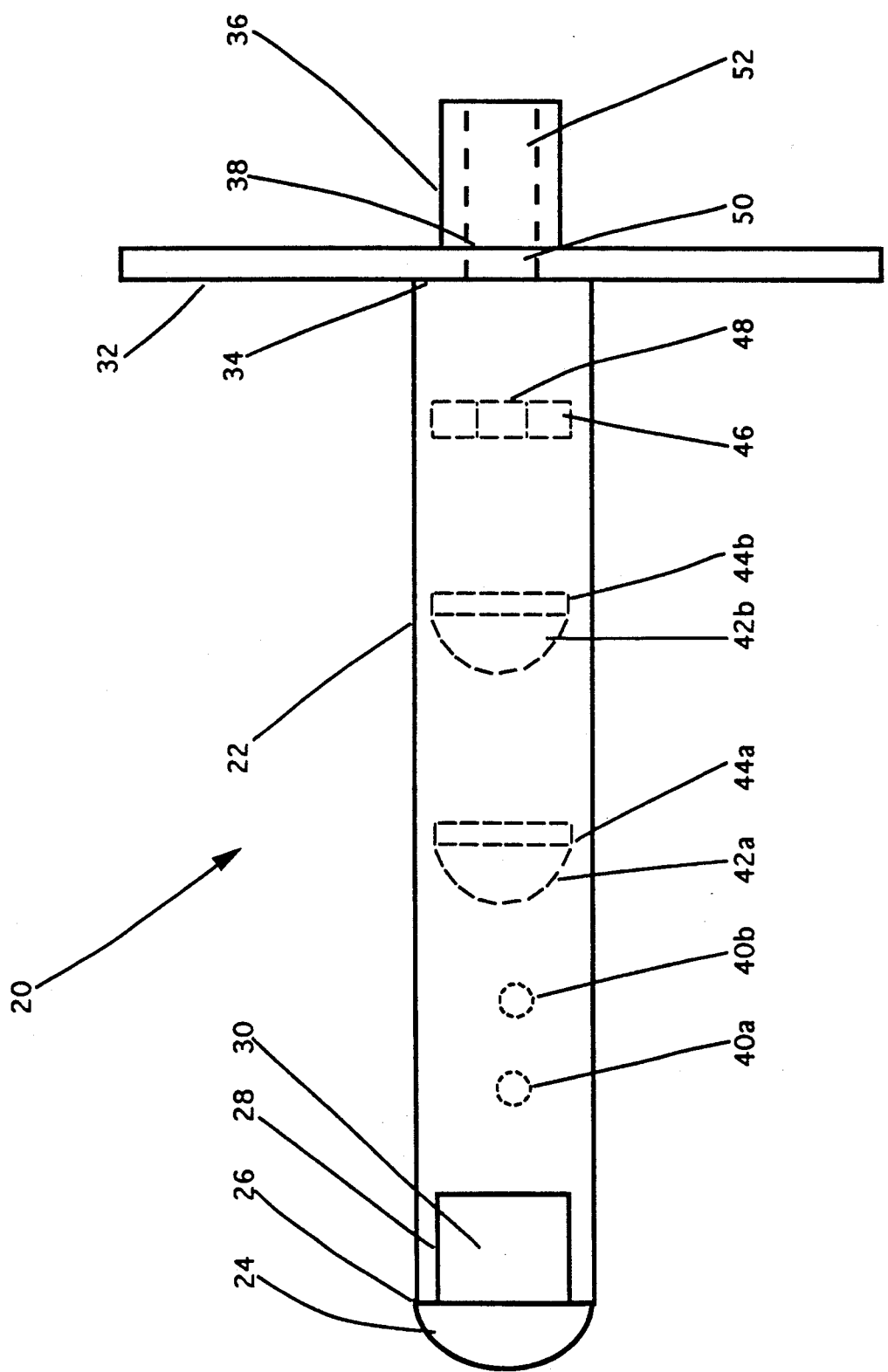
FIG. 1 is a top view of the invention.

Referring now to FIG. 1, sheath 20, the present invention, is shown in top view. Sheath 20, except as specifically noted, is constructed of stainless steel. Generally cylindrical body 22 is welded to end cap 24 at cap joint 26. Rectangular fill port 28, which is an aperture through the upper surface of body 22, is adjacent to end cap 24. Body interior 30, which is partially visible through fill port 28, is a vacant space having a generally cylindrical shape concentric with the longitudinal axis of body 22.

Body 22 is welded to flange 32 at flange joint 34. Flange 32 is welded to union 36 at union joint 38. Flange 32 is disk-shaped and is concentric with the longitudinal axis of body 22. Union 36 has a generally cylindrical shape concentric with the longitudinal axis of body 22. End cap 24 is here defined as the forward-most location on sheath 20 and union 36 is here defined as the rearward-most location on sheath 20.

Certain features of sheath 20 are shown with hidden lines. Drain hole 40a is a circular drain aperture through the lower surface of body 22. Drain hole 40a is relatively small compared to fill port 28, being about 1/20 the size of the latter. Drain hole 40a is located rearward of fill port 28. Drain hole 40b is sized and shaped similarly to drain hole 40a. Drain hole 40b is located rearward of drain hole 40a.

Drain notch 42a is a drain aperture through the lower surface of body 22. Drain notch 42a is approximately semi-circular or semi-eliptical, oriented with the curved portion of its perimeter forward and the straight portion of its perimeter rearward. Drain notch 42a is smaller than fill port 28, being about ¼ the size of the latter. Drain notch 42b is sized, shaped, and oriented similarly to drain notch 42a. Drain notch 42b is located rearward of drain notch 42a.

Weir 44a is a projection within body interior 30 and ascending from the lower surface of body 22. Weir 44a is located immediately rearward of drain notch 42a. Weir 44b, sized, shaped, and oriented similarly to weir 44a, is located immediately rearward of drain notch 44b. Weirs 44a and 44b are welded to body 22. Weirs 44a and 44b, which rise approximately to the lower one-third of body interior 30, will be further described hereinbelow.

Gasket 46 is disk-shaped and made of silicon rubber. Gasket 46 sealably conforms to the interior surface of body 22. Gasket 46 has disk-shaped gasket aperture 48. Gasket aperture 48 is sized so that gasket 46 provides a gas-tight, friction fit around the pH probe. Flange 32 has disk-shaped flange aperture 50. Union 36 has cylindrical, threaded union aperture 52. Flange aperture 50, and union aperture 52 are and have approximately equal diameters adapted to receive a pH probe. Body interior 30, gasket aperture 48, flange aperture 50, and union aperture 52 are all concentric about the longitudinal axis of body 22 to provide a cylindrical passage between body interior 30, gasket aperture 48, flange aperture 50, and union aperture 52 which cylindrical passage is adapted to receive a pH probe.

Figure 2:
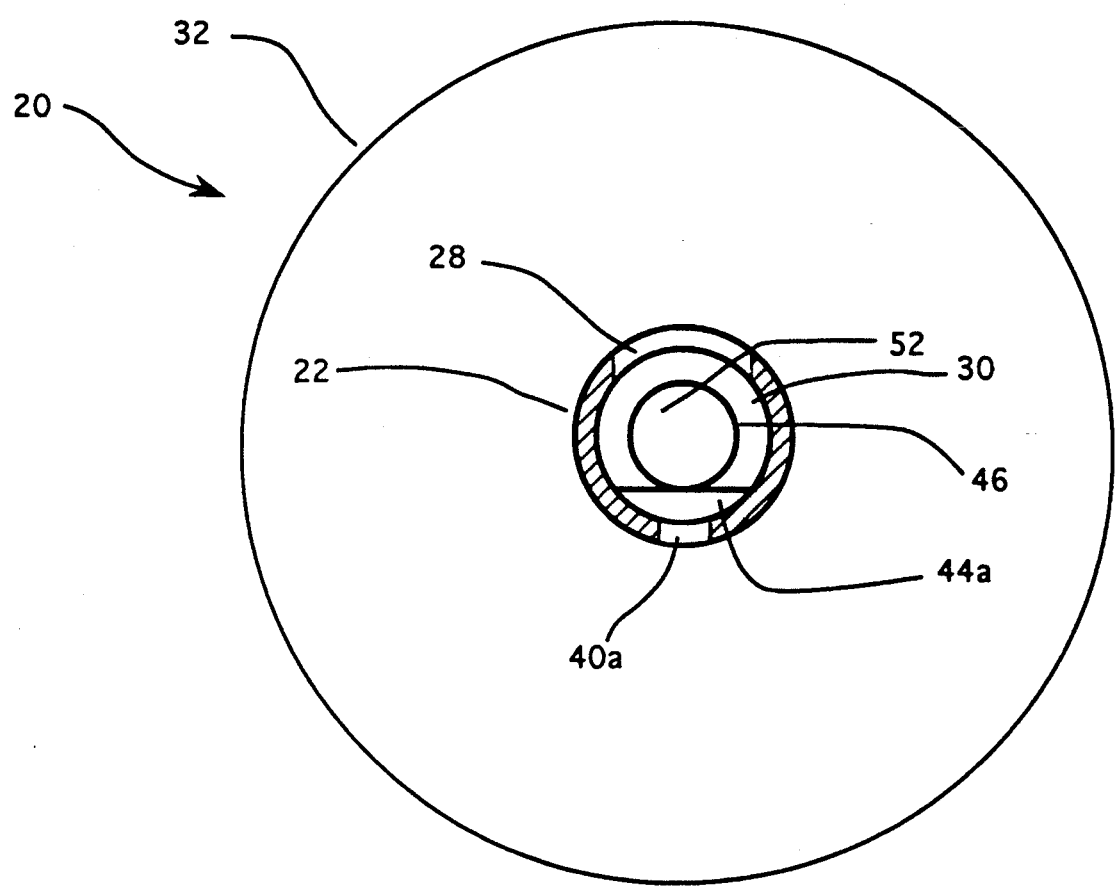
FIG. 2 is a end view of the invention, in partial section.

FIG. 2 provides an end view of sheath 20 with body 22 in partial section. When in situ, sheath 20 is oriented horizontally along its length with fill port 28 high (12:00 o'clock position) and drain holes 40a and 40b oriented low (6:00 o'clock position). (The manner of securing sheath 20 in situ is discussed below.) With Sheath 20 so oriented, drain notches 42a and 42b (not shown) are also oriented low. Accordingly, FIG. 1 and FIG. 2 show sheath 20 in in situ orientation. Relative heights as used herein to describe features of sheath 20 are with respect to such in situ orientation of sheath 20. Weirs 44a and 44b ascend from body 22 to reach the cylindrical passage defined by gasket aperture 48, flange aperture 50, and union aperture 52.

Figure 3:
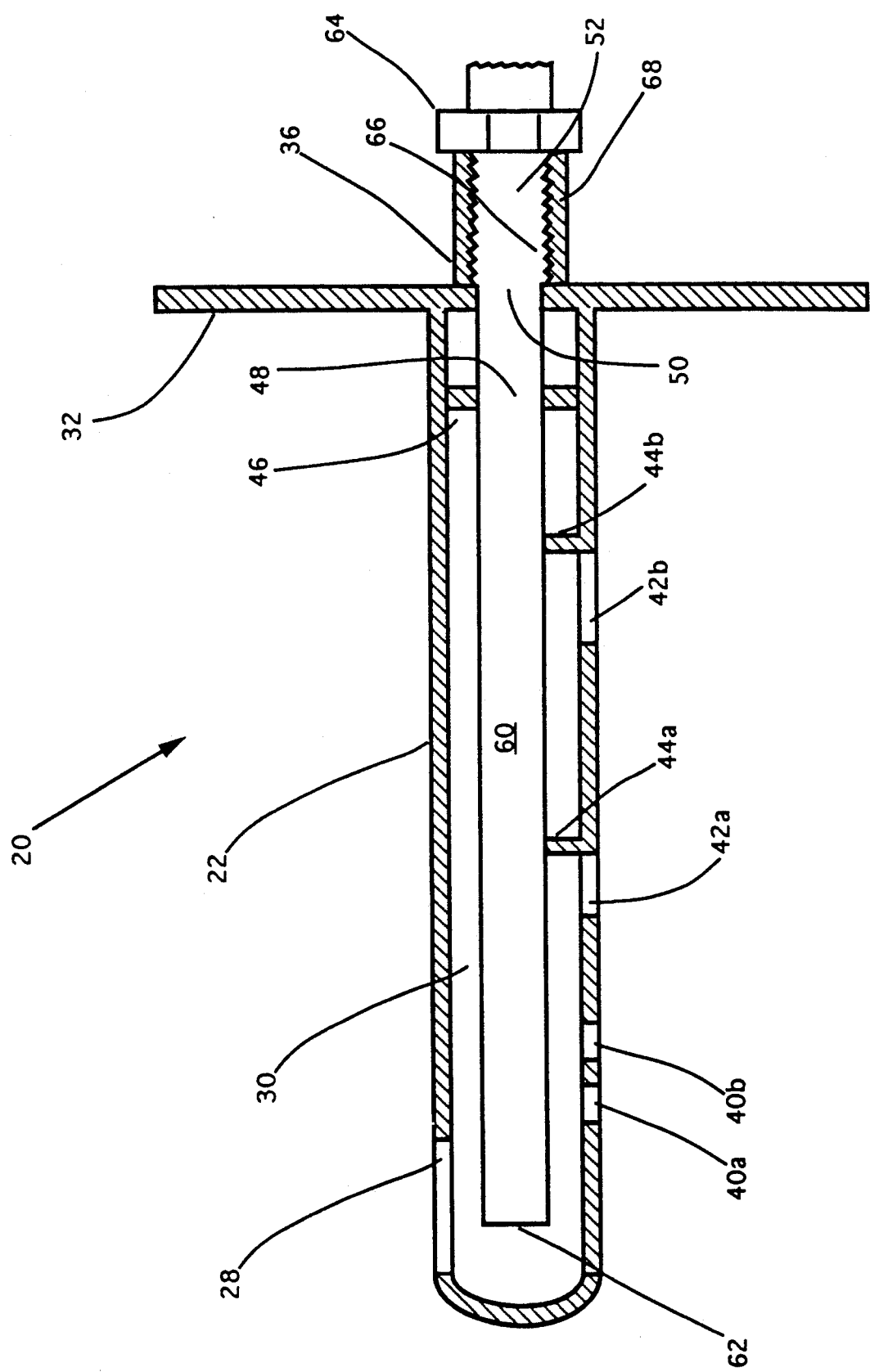
FIG. 3 is a side elevation view, in longitudinal section, of the invention.
Figure 4:
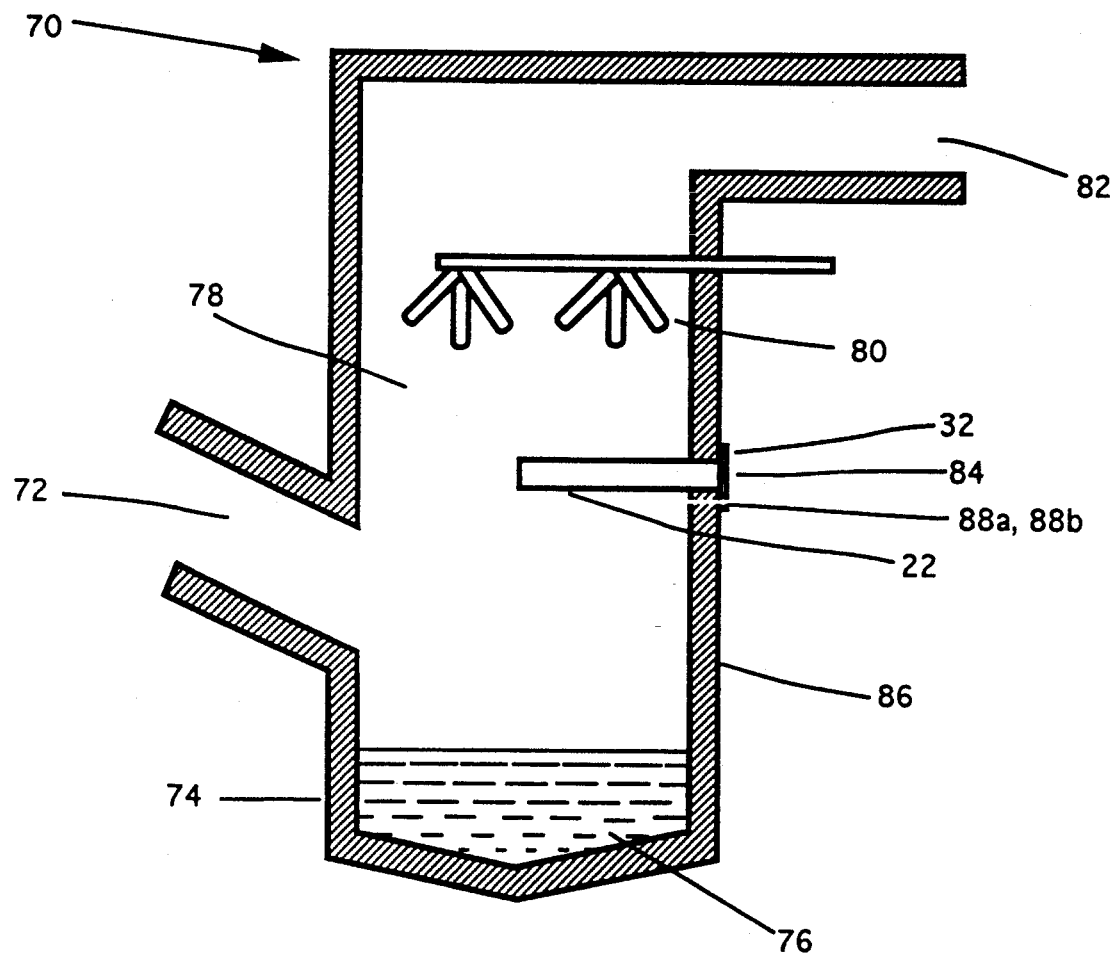
FIG. 4 is a side elevation view, in section, of a conventional absorber in which the invention is used.

FIG. 3 shows sheath 20 in side elevation view, in longitudinal section. This horizontal orientation of sheath 20 provided by FIG. 4 is also in situ orientation. Conventional sensor 60 having an elongated body is used with sheath 20. Sensor 60 is cylindrical. Sensor 60 is inserted into sheath 20 through union aperture 52. So inserted, sensor 60 is concentric with the longitudinal axis of body 22. Sensor 60 extends longitudinally such that electrode 62 is below fill port 28. Sensor 60 has hexagonal nut 64 which is used to screw male threads 66 of sensor 60 into female threads 68 within union aperture 52. Weirs 44a and 44b provide vertical support to sensor 60. Gasket 46 sealably conforms to sensor 60. So installed, sensor 60 occupies union aperture 52, flange aperture 50, and gasket aperture 48.

Referring now to FIG. 4, a conventional absorber 70 is shown in sectional side view with sheath 20 shown in situ. Absorber 70 has gas inlet 72, tank 74 (which, as shown, contains a bulk slurry 76), spray zone 78, sprayer 80, and gas outlet 82. Spray zone 78 is under sprayer 80 and tank 74 is under spray zone 78.

Absorber 70 has an insertion port 84 in absorber wall 86 through which body 22 is inserted so that body 22 is within spray zone 78. This manner of insertion locates sheath 20 in situ, as mentioned above. Insertion port 84 is circular and sized to conform to body 22. Flange 32 has round holes and absorber 70 has corresponding round holes at matched locations surrounding insertion port 84. These matched holes allow sheath 22 to be conventionally bolted to the exterior portion of absorber wall 86. Bolting hole 88a through the flange and matched bolting hole 88b through the absorber are representative of the matched holes.

Function of the Invention

The function of the invention is first illustrated by reference to FIG. 4. When absorber 70 is operating, $SO_2$ laden gas enters absorber 70 by way of gas inlet 72. Gas then ascends through spray zone 78 and continues to ascend past sprayer 80. Gas then exits absorber 70 by way of gas outlet 82.

Sprayer 80 emits a spray which descends through spray zone 78 and further descends to enter tank 74 where it is contained as a bulk slurry 76. As the spray and gas pass through the spray zone 78 they chemically react to change a chemical property of the gas ($SO_2$ removal in this case) and to change chemical properties of the spray. Sheath 20 is installed in spray zone 78 such that sheath 20 is exposed to descending spray travelling through spray zone 78. So installed, elongated sheath body 22 serves as a support member to support fill port 28 at a selected location. The location of sheath 20 in spray zone 78 allows an accurate measurement of pH in the absorber spray zone 78 prior to pH change resulting from the spray leaving the spray zone 78. This pH measurement accurately reflects the complex chemical reactions that occur in the absorber spray zone 78.

The particular location and elevation of the insertion port, into which sheath 20 is inserted into absorber 70, is selected and changed according to the particular portion of the spray zone 78 which is of interest. The elevation for placement of the sheath 20 in spray zone 78 is selected to be above bulk slurry 76 at an elevation of interest. The length of body 22 is also selected according to the particular portion of spray zone 78 which is of interest. Multiple sheaths 20, which vary in length of their body 22, may be used for measuring different horizontal depths from insertion port 84 into spray zone 78.

Thus, by pH monitoring at various locations, elevations, and depths into the absorber, the entire absorber spray zone 78 may be characterized. Multiple sheaths 20, each having a sensor 60, may be used simultaneously for monitoring different locations within spray zone 78. These multiple sheaths 20 would have lengths that would not necessarily be uniform but which would depend upon the different particular locations of interest.

The function of the invention is next described with reference to FIG. 3. As mentioned above, sheath 20 is exposed to descending spray. Fill port 28 collects a portion of the spray as a result of gravitational forces and as a result from pressure of descending spray. Spray pressure arises from impact of spray since spray is forced through nozzles under pressure. Collected spray flows within body interior 30 as a result of gravitational forces and as a result of pressure from descending spray and collected spray accumulates as a slurry sample within body interior 30.

The majority of slurry from the slurry sample is discharged from body interior 30 by way of drain notches 42a and 42b as a result of gravitational forces and as a result of spray pressure. Gravitational forces and spray pressure also cause drain holes 40a and 40b to discharge slurry and keep body interior 30 free of solids deposits. Discharged slurry exits sheath 20 and drops to enter bulk slurry 76 for further use in absorber 70 by recycling. It can be observed that elevation of sheath 20 above bulk slurry 76 prevents slurry from the bulk from entering into the slurry sample.

Initially, spray enters fill port 28 to collect as a sample slurry within interior 30 at a faster rate than slurry is discharged from body interior 30. In steady state operation, however, the sample slurry rises to a height sufficient to immerse electrode 62. In steady state operation, the slurry flows through body interior 30 in a substantially "first-in-first-out" fashion so that a steady stream of new slurry continuously refreshes the sample slurry to pass electrode 62. Electrode 62, the sensing element of sensor 60, senses a chemical property of slurry (pH in this case) as that slurry passes electrode 62. Slurry thus flows through body interior 30 to be discharged from body interior 30 at approximately the same rate at which slurry collects in body interior 30. The rate of slurry flow is determined primarily by spray rate and slurry viscosity as well as the dimensions of fill port 28, body interior 30, drain holes 40a and 40b, and drain notches 42a and 42b. Slurry flow through body interior 30 provides a continuous, fresh slurry sample and provides self-rinsing operation, free of solids deposits.

When electrode 62 becomes immersed in the sample slurry, the sample slurry, the body 22, and the location of fill port 28 jointly act to protect delicate electrode 62 from direct impact of abrasive spray particles and gas contaminants to reduce electrode wear. Body 22 acts as a housing to protect electrode 62 while slurry acts as a cover for electrode 62. This controlled environment for electrode 62 increases the service life of the electrode 62, and reduces the need for maintenance of sensor 60. The rugged sheath 20, constructed of corrosion and erosion resistant materials, provides the controlled environment for the electrode 62, while reducing maintenance and increasing service life of sensor 60.

Weirs 44a and 44b function to create a back pressure on the sample slurry in order to inhibit flow of slurry rearward and to immerse electrode 62. Weirs 44a and 44b also support the delicate sensor 60. Gasket 46 prevents slurry and gases from flowing rearward of gasket 46. A friction-fit of the gasket minimizes leakages against sealing surfaces of gasket 46 and body interior 30 as well as sealing surfaces of gasket 46 and sensor 60.

Sheath 20 normally remains bolted to absorber 70 for extended periods of absorber operation, for months at a time, for example. Sensor 60 may be removed, on a daily or even more frequent basis if necessary, from sheath 20 for calibration, repair, replacement, or for other purposes. Removal is accomplished by withdrawing sensor 60 rearward from union 36 while sheath 20 remains bolted in situ. A conventional ball valve may be used to prevent gas, spray, and slurry from escaping absorber 70 by way of union aperture 52 when sensor 60 has been withdrawn from sheath 20. A conventional gate valve may be used to prevent gas, spray, and slurry from escaping absorber 70 by way of insertion port 84 when sheath 20 has been removed from absorber 70.

The present invention may be modified within the spirit of the present invention to meet site specific or other needs. For example, fill port 30 may be lengthened to collect spray from a long cross section of spray zone 78. Body 22 may be sized such that electrode 62 is relatively more rearward of end cap 24. Additional drain holes 40a or drain notches 42a may be provided or conversely, a single drain hole 40a or a single drain notch 42a may be used. Body 22 may be oriented at an angle below the horizontal. A single sheath 20 may be used to measure different horizontal depths by inserting body 22 to the desired depth and by using spacing means to secure sheath 20 to insertion port 84 while spacing flange 32 from insertion port 84. Such spacing means may be, for example, a cylinder with flanges at both ends and having an interior cylindrical wall sized to receive body 22. Such a spacing means would resemble a spool; one flange would be bolted to insertion port 84 and flange 32 would be bolted to the other flange of the spool.

Persons skilled in the art of the present invention may, upon exposure to the teachings herein, conceive other variations. Such variations are deemed to be encompassed by the disclosure, the invention being limited only by the appended claims.

We claim:

1. In an $SO_2$ absorber comprising a vessel having a means for spraying absorber slurry disposed at an upper end of said vessel, a flue gas inlet at a lower end of said vessel, and a flue gas outlet at said upper end above said spray means, an apparatus for measuring a process control variable, said apparatus comprising:
   an absorber wall defining a spray zone within said $SO_2$ absorber vessel between said spray means and said inlet, said absorber wall having an insertion port;
   a sheath inserted into said spray zone by way of said insertion port and attached to said absorber wall, said sheath having a sheath interior, a spray fill port, a slurry drain, and a sensor passage, said spray fill port positioned to collect a descending spray portion into said sheath interior by way of said spray fill port, said sheath interior adapted to accumulate a slurry sample, said slurry drain positioned to drain from said sheath interior said slurry from said sample;
   a sensor having an electrode for measuring said process control variable, said sensor inserted into said sheath interior by way of said sensor passage, said electrode immersed in said slurry sample.

2. The apparatus of claim 1 wherein said spray fill port is adapted to continuously collect said spray portion.

3. The apparatus of claim 2 wherein said slurry drain is adapted to continuously drain said slurry from said sample.

4. The apparatus of claim 3 wherein said spray fill port, said sheath interior and said slurry drain are adapted to collect said spray portion and to drain said slurry in a first-in-first-out fashion such that said slurry sample is continuously refreshed with new slurry.

5. The apparatus of claim 4 wherein said sheath is elongated to support said spray fill port at a selected distance from said absorber wall.

6. The apparatus of claim 5 wherein said sheath support member further comprises a sensor fastener located near said insertion port, wherein said sensor further comprises a sheath fastener, wherein said sensor fastener and said sheath fastener are adapted to permit said sensor to be removably fastened to said sheath.

7. The apparatus of claim 6 wherein said sensor further comprises an elongated sensor body with said electrode at a first end of said sensor body and said sheath fastener at a second end of said sensor body.

8. The apparatus of claim 7 wherein said sheath further comprises a weir and wherein said weir is adapted to vertically support said sensor body.

9. The apparatus of claim 8 wherein said slurry drain is located adjacent to said weir.

10. The apparatus of claim 9 wherein said slurry drain is located between said electrode and said weir.

11. The apparatus of claim 1 wherein said process control variable is a pH of said slurry sample.

12. The apparatus of claim 1 wherein gravitational forces causes said slurry to flow within said sheath interior.

13. The apparatus of claim 1 wherein gravitational force causes said slurry to flow from said sheath interior through said slurry drain.

14. The apparatus of claim 1 wherein spray pressure causes said slurry to flow within said sheath interior.

15. The apparatus of claim 1 wherein spray pressure causes said slurry to flow from said sheath interior through said slurry drain.

16. The apparatus of claim 4 wherein gravitational force causes said slurry to flow within said sheath interior.

17. The apparatus of claim 4 wherein gravitational force causes said slurry to flow from said sheath interior through said slurry drain.

18. The apparatus of claim 4 wherein spray pressure causes said slurry to flow within said sheath interior.

19. The apparatus of claim 4 wherein spray pressure causes said slurry to flow from said sheath interior through said slurry drain.

20. The apparatus of claim 11 wherein gravitational force causes said slurry to flow within said sheath interior.

21. The apparatus of claim 11 wherein gravitational force causes said slurry to flow from said sheath interior through said slurry drain.

22. The apparatus of claim 11 wherein spray pressure causes said slurry to flow within said sheath interior.

23. The apparatus of claim 11 wherein spray pressure causes said slurry to flow from said sheath interior through said slurry drain.

* * * * *